US005352807A

United States Patent [19]
Shih

[11] Patent Number: 5,352,807
[45] Date of Patent: Oct. 4, 1994

[54] PROPYLENE OXIDE PURIFICATION

[75] Inventor: T. Thomas Shih, Bryn Mawr, Pa.

[73] Assignee: ARCO Chemical Technology, L.P., Wilmington, Del.

[21] Appl. No.: 147,253

[22] Filed: Nov. 4, 1993

Related U.S. Application Data

[63] Continuation-in-part of Ser. No. 936,965, Aug. 28, 1992, abandoned, which is a continuation-in-part of Ser. No. 839,985, Feb. 20, 1992, Pat. No. 5,187,287.

[51] Int. Cl.⁵ .................. C07D 301/32; C07D 303/04
[52] U.S. Cl. ..................................................... 549/542
[58] Field of Search ........................................ 549/542

[56] References Cited

U.S. PATENT DOCUMENTS

| | | |
|---|---|---|
| 2,550,847 | 5/1951 | Mitchell et al. ............... 549/542 |
| 2,622,060 | 12/1952 | Robeson et al. . |
| 2,847,480 | 8/1958 | Kaiser ........................... 568/917 |
| 3,350,417 | 10/1967 | Binning et al. . |
| 3,351,635 | 11/1967 | Kollar . |
| 3,477,919 | 11/1969 | Lichtenwalter et al. . |
| 3,578,568 | 5/1971 | Washall . |
| 3,838,020 | 9/1974 | Kageyama et al. . |
| 3,843,488 | 10/1974 | Schmidt et al. . |
| 3,881,996 | 5/1975 | Schmidt . |
| 3,904,656 | 9/1975 | Broz . |
| 3,909,366 | 9/1975 | Schmidt et al. . |
| 4,140,588 | 2/1979 | Schmidt . |
| 4,691,034 | 9/1987 | Sanderson et al. . |
| 4,691,035 | 9/1987 | Sanderson et al. ............ 549/542 |
| 4,692,535 | 9/1987 | Larson et al. . |
| 5,000,825 | 3/1991 | Shih et al. . |
| 5,006,206 | 4/1991 | Shih et al. . |
| 5,187,287 | 2/1993 | Shih ............................... 549/542 |

FOREIGN PATENT DOCUMENTS

| | | |
|---|---|---|
| 1300537 | 8/1969 | Fed. Rep. of Germany ...... 568/917 |
| 118873 | 3/1976 | Fed. Rep. of Germany . |

Primary Examiner—Joseph E. Evans
Attorney, Agent, or Firm—William C. Long

[57] ABSTRACT

The method for the separating close-boiling impurities from propylene oxide essentially free of high molecular weight poly (propylene oxide) which comprises contacting the impure propylene oxide with solid activated carbon adsorbent and separating propylene oxide reduced in impurities content from the adsorbent.

1 Claim, No Drawings

PROPYLENE OXIDE PURIFICATION

RELATED APPLICATIONS

This application is a continuation-in-part of copending application Ser. No. 07/936,965 filed Aug. 28, 1992, now abandoned which is a continuation-in-part of application Ser. No. 07/839,985 filed Feb. 20, 1992, now U.S. Pat. No. 5,187,287.

BACKGROUND OF THE INVENTION

1. Field of the Invention

The present invention relates to the separation of various difficulty separable close-boiling impurities such as esters, aldehydes, ketones and hydrocarbons from propylene oxide by treatment with solid activated carbon adsorbent.

2. Description of the Prior Art

Alkylene oxides such as propylene oxide are highly important chemicals useful in a great number of applications. An important commercial technology for producing the alkylene oxides is via the catalytic reaction between the corresponding olefin and an organic hydroperoxide, the hydroperoxide being prepared by hydrocarbon oxidation. See, for example, U.S. Pat. No. 3,351,635.

Ethylene oxide is generally prepared by silver catalyzed molecular oxygen oxidation of ethylene. The lower alkylene oxides contain impurities which are difficult to separate due to small differences in boiling point between the alkylene oxide and the impurities. In the case of propylene oxide, for example, considerable effort has been devoted to separating close boiling methyl formate, acetaldehyde, propionaldehyde, $C_4$–$C_7$ hydrocarbons especially $C_6$ hydrocarbons, and other impurities. Ethylene oxide has associated with it impurities such as formaldehyde while butylene oxide generally is contaminated with impurities such as methyl acetate, ethyl acetate, acetone, methyl ethyl ketone, methanol and hydrocarbons, especially $C_6$–$C_8$ hydrocarbons.

One direction taken by prior workers has been to provide extractive distillation techniques to accomplish the separation. U.S. Pat. No. 3,838,020 shows a dual solvent extractive distillation process. U.S. Pat. No. 3,843,488 shows extraction distillation using a $C_8$ to $C_{20}$ hydrocarbon to purify propylene oxide. U.S. Pat. No. 3,909,366 shows extractive distillation purification of propylene oxide using $C_6$ to $C_{12}$ aromatic hydrocarbon. U.S. Pat. No. 4,140,588 uses water in extractive distillation purification of propylene oxide. U.S. Pat. No. 3,881,996 uses plural stage distillation to purify propylene oxide. East German Patent Specification 118,873 uses aliphatic alcohols such as tertiary butanol in separating methyl formate from propylene oxide by extractive distillation. U.S. Pat. No. 5,006,206 uses tertiary butyl alcohol and water in the extractive distillation purification of propylene oxide.

It has previously been proposed to separate oxygen-containing impurities from the propylene oxide by extractive distillation using lower glycols such as ethylene glycol and propylene glycol. See U.S. Pat. No. 3,578,568 which describes this procedure and which teaches use of solvent in amount to comprise 15 to 50% of the vapor space in the distillation zone. U.S. Pat. No. 5,000,825 describes a similar separation but one which uses much lower solvent concentrations whereby propylene oxide losses are reduced.

U.S. Pat. No. No. 3,477,919 teaches a method for purifying propylene oxide contaminated with impurities such as methyl formate which boil near propylene oxide. The methyl formate impurity is removed from the contaminated propylene oxide by reaction with an aqueous slurry of calcium hydroxide.

U.S. Pat. No. 2,622,060 teaches a process for separating propylene oxide from a crude reaction mixture by treatment with an aqueous alkali metal hydroxide solution.

U.S. Pat. No. 2,550,847 teaches a process for the purification of propylene oxide in a crude reaction mixture containing methyl formate by subjecting the mixture to strong agitation with an aqueous solution of an alkaline saponifying agent.

U.S. Pat. No. 3,350,417 teaches a process for purifying propylene oxide comprising parallel and serial stages of distillation and a caustic treatment to simultaneously aldolize acetaldehyde and saponify methyl formate. The solvent used in the reaction step is removed before subsequent caustic treatment.

U.S. Pat. No. 4,691,034 removes methyl formate from propylene oxide by contact with an aqueous calcium hydroxide slurry to which a solubilizer has been added. U.S. Pat. No. 4,691,035 removes methyl formate from propylene oxide by contact with a base such as sodium hydroxide in water and glycerol.

A problem with prior procedures which involve distillation separation of impurities such as $C_6$ hydrocarbons from propylene oxide is that, at the elevated temperatures necessary to carry out the distillation, additional impurities are formed. For example, at the distillation temperatures, non-volatile high molecular weight ethers are formed which require a separate treatment for removal.

U.S. Pat. No. 4,692,535 shows such removal of non-volatile high molecular weight ethers from propylene oxide by treatment with an absorbent such as activated carbon, for example.

U.S. Pat. No. 3,904,656 shows treatment of an ethylene oxide stripper bottoms with ion exchange materials to remove metal salts and with activated carbon to remove ultra-violet light absorbers. The stripper bottoms treated are primarily comprised of water and ethylene glycol and usually contain at most extremely minor amounts of ethylene oxide, e.g. less than 0.1 wt. %.

Despite the efforts of prior workers, work has continued in an effort to further improve the separation of close-boiling contaminating impurities such as $C_4$–$C_8$-hydrocarbons, esters such as methyl formate and methyl acetate, aldehydes such as acetaldehyde and propionaldehyde, ketones such as acetone and methyl ethyl ketone, alcohols such as methanol, and the like from propylene oxide.

BRIEF DESCRIPTION OF THE INVENTION

In accordance with the present invention, it has been found that propylene oxide containing close-boiling impurities can be purified by contact with solid activated carbon adsorbent. By this procedure, extractive distillation purification can be avoided, thus greatly simplifying propylene oxide purification while at the same time the formation of additional impurities including high-boiling ethers is minimized.

DETAILED DESCRIPTION OF THE INVENTION

This invention is especially applicable to the purification of propylene oxide prepared, for example, by reaction of an organic hydroperoxide with propylene and containing methyl formate, acetaldehyde, propionaldehyde and/or $C_4$-$C_7$ hydrocarbon contaminants, illustratively each in amounts of 50 to 1600 ppm by weight, usually 100 to 800 ppm on a water-free basis. The propylene oxide treated according to the invention may contain in addition to the propylene oxide and impurities up to about 95 wt.% water but usually comprise at least 50 wt. % propylene oxide and most usually at least 95 wt. % propylene oxide.

Propylene oxide treated in accordance with the present invention contains the close-boiling impurities described above and contains essentially no high-boiling ethers, i.e. less than 0.05 ppm by weight high-boiling ethers. U.S. Pat. No. 4,692,535 to Larson, et al. provides a process for separating poly (propylene oxide) having molecular weight of at least 50,000 from propylene oxide by treatment with an adsorbent such as activated carbon. The high molecular weight polymers separated by Larson, et al. are formed as a result of propylene oxide being subjected to elevated temperatures for prolonged periods, especially in contact with carbon steel. See examples 4 and 5 of Larson, et al.

Generally, propylene oxide produced by conventional technology such as the oxirane hydroperoxide process contains close-boiling impurities as above described but contains no significant amount of poly (propylene oxide) polymer having molecular weight above 50,000, i.e. less than 0.05 ppm by weight of such polymer, and it is this propylene oxide which is purified in accordance with the present invention.

In accordance with the present invention, a liquid mixture comprising propylene oxide and close-boiling contaminants is contacted with solid activated carbon adsorbent. As a result of this contact, the contaminants are selectively adsorbed by the adsorbent and propylene oxide substantially reduced in contaminant content is recovered. The adsorbent can be regenerated by burning in air after the contaminant removal function has decreased to an unsatisfactory level.

The invention may be carried out in a continuous or batch-wise fashion in accordance with known procedures. Continuous operation is preferred as is the use of a plurality of adsorbent contact zones with one zone being in use while adsorbent in a second is being regenerated. The use of three contact zones is particularly preferred, with two zones in use at the same time, one a lead contact zone and the second a polishing zone, while the third zone is being regenerated.

Conditions for the contact involve temperatures in the range of about 10 to 50° C., preferably 15 to 25° C., although temperatures outside these ranges can be used.

Generally, the use of about 0.0001 to about 0.1, preferably 0.001 to about 0.01 grams of solid absorbent per gram of propylene oxide being treated will give satisfactory results. Contact time in the range of from about 1 to about 60 minutes, preferably 2 to 30 minutes, will provide sufficient solid adsorbent treatment to attain the objectives of the method of this invention.

Exceptionally useful activated carbons or charcoals include those obtained from lignite, gas black, coconut, bagasse, wood, sawdust, peat, pulp-mill waste, blood, bone, etc. Specific activated carbons include Calgon Corporation granular carbons such as Calgon F 400. NORIT granular activated carbons such as NORIT C, Cenco activated carbons, products of Central Scientific Company, Nuchar activated carbons, products of West Virginia Pulp and Paper Company, and products of Darco Division, ICI AMERICAS, Inc. Rohm and Haas Ambersob carbonaceous adsorbents such as X-340 and the like can be employed as can Rohm and Haas activated Amberlite. Illustrative commercially available carbons include Type CAL granular carbon (Calgon Corporation) and NORIT RO.8 granular activated carbon (NORIT Corporation).

Adsorption is preferably carried out by passing the impure propylene oxide through a bed of granular activated carbon. Alternatively, powdered activated carbon can be slurred in the impure propylene oxide and separated by filtration.

The following examples illustrate the invention:

EXAMPLE 1

A ¾" ID and 8"-long column packed with 40 grams of solid adsorbent activated carbon (Calgon F 400) was used in a series of adsorption experiments for impurities removal from crude propylene oxide. A crude propylene oxide stream essentially free of poly (propylene oxide) having at least 50,000 molecular weight, i.e. less than 0.05 ppm by weight, and containing as impurities 480 ppm by weight acetaldehyde, 0.3 wt. % methanol, 775 ppm by weight methyl formate, 775 ppm by weight propionaldehyde, 0.41 wt. % acetone, and 450 ppm by weight $C_6$ hydrocarbons including 300 ppm 2-methyl pentane, 2-methyl-2-pentene and 2-methyl-1-pentene was fed into the top of the column at 100 cc/hr. The column was maintained at ambient temperature (25° C.) and pressure (1 atmosphere). The effluent from the bottom of the column was collected and sampled for GC analysis. After 5 hours of operation, the accumulative effluent with a total volume of about 500 cc contained non-detectable (5 ppm or less) amounts of acetaldehyde, methyl formate, propionaldehyde, $C_6$ hydrocarbons, about 0.24 wt. % methanol and about 0.38 wt. % acetone. The concentration breakthrough for acetone occurred at about 26 minutes, for methanol at about 50 minutes, for acetaldehyde at about 4.1 hours, for methyl formate at about 5 hours, for propionaldehyde at about 6 hours and for $C_6$ hydrocarbons at about 8 hours.

The results showed that impurities such as acetaldehyde, methyl formate, propionaldehyde and especially $C_6$ hydrocarbons are selectively and effectively removed from crude propylene oxide, and high purity propylene oxide can be produced according to the invention.

In accordance with the present process it is possible to purify propylene oxide which contains close-boiling impurities without resorting to extractive distillation procedures which introduce added expense and complexity and which actually tend to result in additional impurities formation.

Hydrocarbons, which are key impurities, can be separated especially effectively through practice of the invention.

What is claimed is:

1. The method of purifying propylene oxide prepared by reaction of an organic hydroperoxide with propylene and containing less than 0.05 ppm by weight of poly (propylene oxide) having a molecular weight of at least 50,000 and containing contaminating amounts of one or more of methyl formate, acetaldehyde, propionaldehyde and $C_4$-$C_7$ hydrocarbon impurities which comprises contacting a liquid mixture of said propylene oxide and impurity with a solid activated carbon absorbent and separating propylene oxide having a reduced impurity content from the absorbent.

* * * * *